United States Patent
Bengtsson (10) Patent No.: US 7,965,851 B2
(45) Date of Patent: Jun. 21, 2011

(54) MODULAR WIRELESS AUDITORY TEST INSTRUMENT WITH INTELLIGENT TRANSDUCERS

(75) Inventor: Stefan Bengtsson, Smoerum (DK)

(73) Assignee: GN ReSound A/S (DK)

( * ) Notice: Subject to any disclaimer, the term of this patent is extended or adjusted under 35 U.S.C. 154(b) by 2380 days.

(21) Appl. No.: 10/394,785

(22) Filed: Mar. 21, 2003

(65) Prior Publication Data
US 2004/0184618 A1 Sep. 23, 2004

(51) Int. Cl.
H04R 25/00 (2006.01)
A61B 5/00 (2006.01)

(52) U.S. Cl. .......................................... 381/60; 600/559
(58) Field of Classification Search .................. 381/60; 600/559; 73/585; 702/103–104, 116
See application file for complete search history.

(56) References Cited

U.S. PATENT DOCUMENTS

| | | | |
|---|---|---|---|
| 5,197,332 A * | 3/1993 | Shennib | 73/585 |
| 5,864,781 A | 1/1999 | White | 702/182 |
| 5,884,202 A | 3/1999 | Arjomand | 701/29 |
| 5,931,791 A | 8/1999 | Saltzstein et al. | 600/513 |
| 5,944,659 A | 8/1999 | Flach et al. | 600/300 |
| 5,987,519 A | 11/1999 | Peifer et al. | 709/230 |
| 6,013,108 A | 1/2000 | Karolys et al. | 792/189 |
| 6,055,487 A | 4/2000 | Margery et al. | 702/84 |
| 6,126,608 A | 10/2000 | Kemme et al. | 600/459 |
| 6,178,527 B1 | 1/2001 | Vidales | 714/44 |
| 6,213,942 B1 | 4/2001 | Flach et al. | 600/300 |
| 6,238,344 B1 | 5/2001 | Gamelsky et al. | 600/437 |
| 6,241,673 B1 | 6/2001 | Williams | 600/437 |
| 6,377,223 B1 | 4/2002 | Clapp et al. | 343/718 |
| 6,440,072 B1 | 8/2002 | Schuman et al. | 600/437 |
| 7,650,004 B2 * | 1/2010 | Durant | 381/312 |
| 2002/0165466 A1* | 11/2002 | Givens et al. | 600/559 |
| 2003/0030342 A1* | 2/2003 | Chen et al. | 310/102 R |
| 2003/0065276 A1* | 4/2003 | Akita | 600/559 |
| 2004/0037428 A1* | 2/2004 | Keller | 381/60 |
| 2004/0071295 A1* | 4/2004 | Wasden et al. | 381/60 |
| 2004/0125758 A1* | 7/2004 | Hayduk | 370/310 |

* cited by examiner

Primary Examiner — Xu Mei
(74) Attorney, Agent, or Firm — Vista IP Law Group, LLP.

(57) ABSTRACT

A method and apparatus for performing various auditory tests utilizing a hand-held, portable, wireless testing device is provided. Within the device is a diagnostic subsystem used to implement and analyze selected tests. Attached to the device, either directly or via a flexible cable, are one or more probes. A processor, storage means, input means and display means are included, thus allowing the device to process and store instructions as well as process, store and display data. A wireless networking subsystem is included, enabling the device to communicate with other, similarly enabled, systems and devices within the device's communication range. Due to the inclusion of the wireless networking subsystem, the device can be configured to allow the user to transmit and/or print data, connect to a network, obtain device configuration updates, and send and receive patient and office updates.

32 Claims, 10 Drawing Sheets

MODULAR WIRELESS AUDITORY TEST INSTRUMENT WITH INTELLIGENT TRANSDUCERS

FIELD OF THE INVENTION

The present invention relates generally to auditory test instruments and, more particularly, to portable, wireless auditory test instruments.

BACKGROUND OF THE INVENTION

Auditory test instruments are generally designed to be mounted to, or maintained on, a desktop. Such instruments often include a display, thus allowing the user to configure the instrument, set the test procedure and/or view the test results. A printer may also be included, thus allowing a hard copy of the test results to be printed. The instrument may also be capable of being connected, for example via an RS-232 connection, to a network, external computer or printer. Examples of such auditory test instruments are those manufactured by GN Otometrics under the Danplex, Madsen, Rastronics, Hortmann and ICS Medical brands.

Although the prior art auditory test instruments perform well, there are several disadvantages associated with them, primarily due to their size. First, as they are somewhat difficult to move from location to location, a single office complex may require multiple instruments, one per testing facility (e.g., one for each examination room). If one of the instruments malfunctions, or if the office complex is trying to minimize costs by limiting the number of instruments per complex, the instrument either has to be physically moved between examination rooms or the patients have to be screened and/or diagnosed in a single room, either way limiting the number of patients that can be screened and/or diagnosed within a given time period. Second, these instruments offer limited portability, thus making it difficult to perform tests outside of the facility in which they are normally used, for example at a hospital, patient's home, etc. Third, the instrument must be located near a suitable power source. Fourth, in order to use the instrument with a separate computer and/or printer, the instrument must be located near the computer and/or printer, or near a suitable network connection.

In addition to the afore-mentioned disadvantages, the previous auditory test instruments are specialized, thus offering no patient and/or office management tools. Accordingly, there is a need for a test instrument that overcomes the disadvantages of the previous test instruments while offering expanded capabilities. The present invention provides such a device.

SUMMARY OF THE INVENTION

The present invention provides a method and apparatus for performing a variety of auditory tests utilizing a hand-held, portable, wireless testing device. Within the device is a diagnostic subsystem which is used to implement selected tests as well as analyze the results of the selected tests. Although the diagnostic subsystem can be fully integrated into the device, preferably it is modular in design, thus allowing the subsystem to be easily replaced as needed to perform system upgrades, testing suite changes, or simple repairs.

In order to perform a specific test, one or more probes are attached to the device, either directly or via a flexible cable. Preferably the probe(s) is an intelligent probe that is capable of communicating data other than stimulus signals and response data. Examples of data that can be communicated with the intelligent probe include calibration data, configuration data, and operational information.

The device of the invention includes at least one processor, storage means (e.g., volatile and/or non-volatile memory), user input means and display means, thus allowing the device to process and store instructions as well as process, store and display data. Additionally, in at least one embodiment the processor, storage means, user input means and display means are used to provide the user with a means of interacting with a data bank. The data bank can be used to store test protocols, instrument configuration files, patient profiles, previous test data, appointment schedules, patient contact information, employee information, patient payment histories, office invoices, etc.

Another subsystem of the device is a wireless networking subsystem that allows the device to communicate with other, similarly enabled, devices within the system's range. Examples of devices and systems that can be enabled and used with the invention are printers, facsimile devices, computers, cellular telephones, personal digital assistants (i.e., PDAs), and LAN systems. Accordingly, the user is able to transmit data, print data, connect to a network, obtain device configuration updates, etc. In at least one embodiment, the wireless networking subsystem also allows the user to send and receive patient and office updates, such as appointment reminders, scheduling changes, etc.

A further understanding of the nature and advantages of the present invention may be realized by reference to the remaining portions of the specification and the drawings.

DESCRIPTION OF THE SPECIFIC EMBODIMENTS

Figure 1:
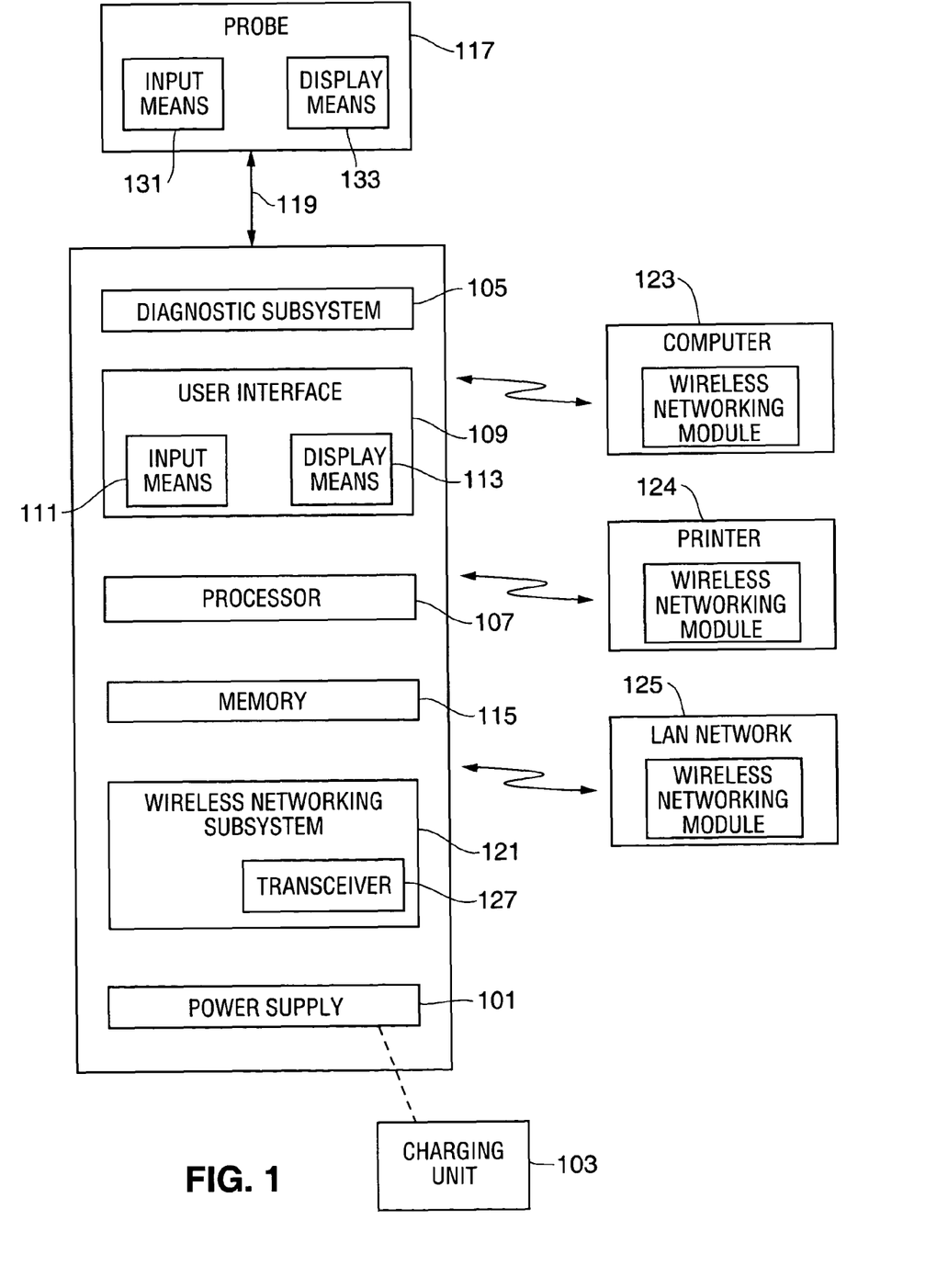
FIG. 1 is a block diagram of a wireless test instrument in accordance with one embodiment of the invention.

FIG. 1 is a block diagram of a wireless auditory test instrument 100 in accordance with one embodiment of the invention. Instrument 100 is designed to be completely portable and preferably small enough and light enough to easily hold in one hand. Given the requirements for portability, instrument 100 includes an internal power supply 101. Power supply 101 can utilize replaceable batteries or rechargeable batteries. If rechargeable batteries are used, they can either be recharged by removal and insertion into a separate battery charger, charged using an internally housed charging circuit temporarily coupled to an external power source, or, as in a preferred embodiment, recharged while housed within instrument 100 using an external charging circuit/unit 103. Although external charging circuit/unit 103 can utilize contacts to electrically couple to internal power supply 101, preferably a contactless method of coupling to internal power supply 101 is used. As such methods are well known in the art, further description of the charging circuit/unit 103 is not provided herein.

Within instrument 100 is a diagnostic subsystem 105 which can be configured for either screening or diagnostic testing. As will be later described in detail, diagnostic subsystem 105 is configurable to perform one or more of a variety of audiometric tests as well as to gather response data. It will be appreciated that diagnostic subsystem 105 is not necessarily a specific module, rather it is representative of the diagnostic capabilities incorporated into instrument 100. Accordingly, the inventors have conceived of an instrument 100 that can utilize any of a variety of multiple, preferably interchangeable, diagnostic subsystems, thus allowing the end user to select the desired testing capabilities. Alternately, a diagnostic subsystem 105 can be used within instrument 100 that can be configured to perform one or more tests selected from a variety of tests.

Instrument 100 includes a processor 107. As used herein, the term processor refers to processors, digital signal processors (DSPs), microprocessors, CPUs, application specific integrated circuits (ASICs), etc. Processor 107 is used to implement tests, analyze test results, and, in general, manage instrument 100's operation. It will be appreciated that instrument 100 can utilize a single processor or multiple processors. For example, although FIG. 1 shows a single processor 107 separate from diagnostic subsystem 105, it is understood that diagnostic subsystem can also include a separate processor. Alternately, instrument 100 can utilize one or more processors that are embedded in diagnostic subsystem 105. Accordingly it will be understood that processor 107 in FIG. 1 is only representative of the processing capabilities included in instrument 100.

A user interface 109 provides the user of instrument 100 with a means of entering commands, thus allowing test parameters to be input, testing to be initiated, test results to be analyzed and/or reviewed, etc. User interface 109 also provides a means by which the user can access other features of instrument 100 (e.g., office management tools, patient management tools, data storage, patient histories, etc.) as well as modify the functionality of instrument 100. User interface 109 includes an input means 111 and a display means 113.

Integrated into instrument 100 is a memory 115. Memory 115 is used to store user preferences in general and test parameters in particular. Preferably memory 115 is also used to store test data. In addition, memory 115 can be used to store patient information (e.g., test histories), office management data (e.g., appointments), and communication protocols with wirelessly connected devices. Preferably memory 115 is comprised of both non-volatile memory (e.g., ROM) and volatile memory (e.g., RAM).

Coupled to instrument 100 is a probe 117. Preferably probe 117 is coupled to instrument 100 by a flexible cable 119. Alternately, probe 117 can be coupled directly to the housing of instrument 100. Regardless of whether probe 117 is coupled via cable 119 or integrated directly into the instrument's housing, preferably it is easily detached and replaced with other probes. It will be appreciated that probe 117 is only representative of a probe in general and that, in fact, any of a variety of probe types and configurations can be used with the preferred embodiment of the invention. Additionally, probe 117 may be comprised of a single probe or of multiple probes.

In order to provide instrument 100 with the desired functionality, it includes a short range wireless networking subsystem 121. Wireless networking subsystem 121 allows instrument 100 to communicate with other similarly enabled devices that are within the system's range. Examples of such devices include computers 123, printers 124, and networks 125.

Figure 2:
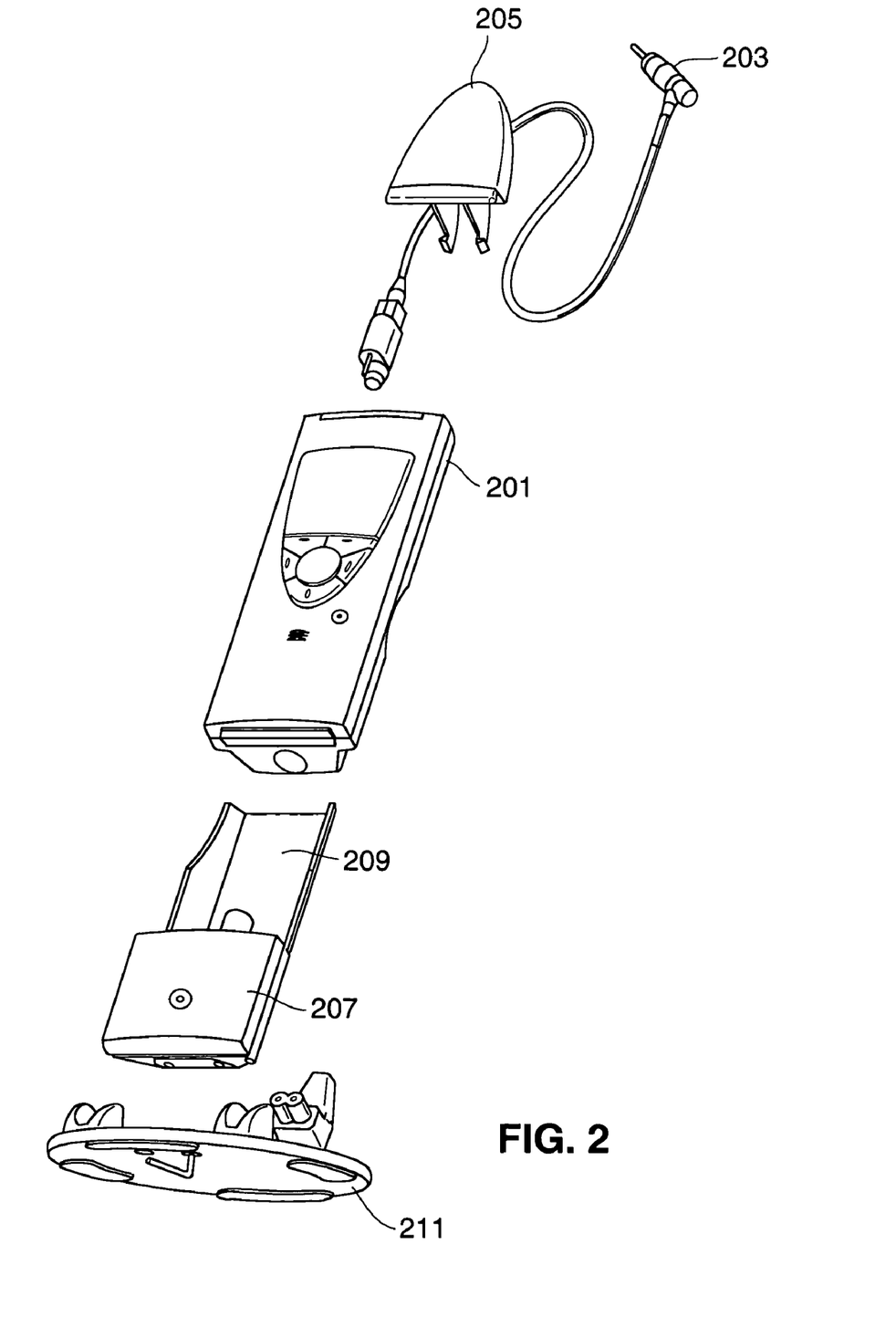
FIG. 2 is a perspective view of a preferred embodiment of the invention.
Figure 3:
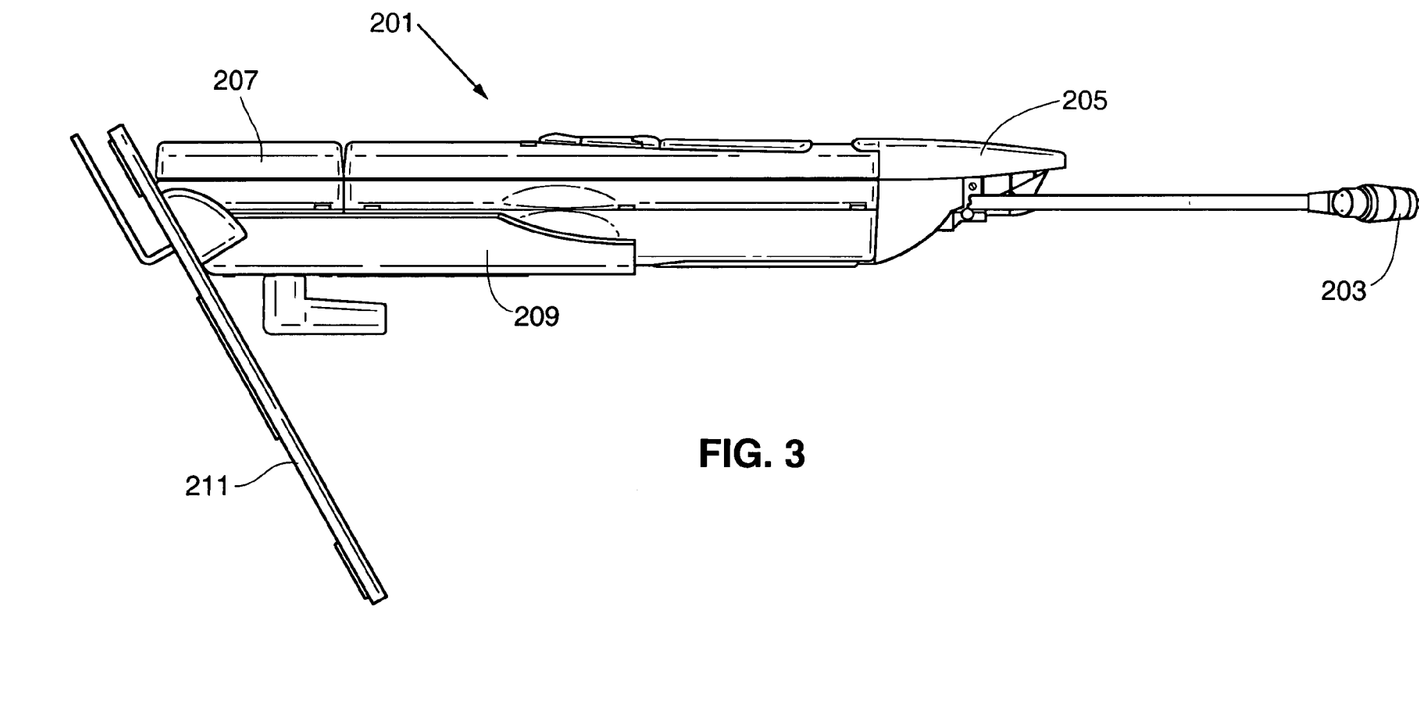
FIG. 3 is a side view of the instrument system shown in FIG. 2.
Figure 4:
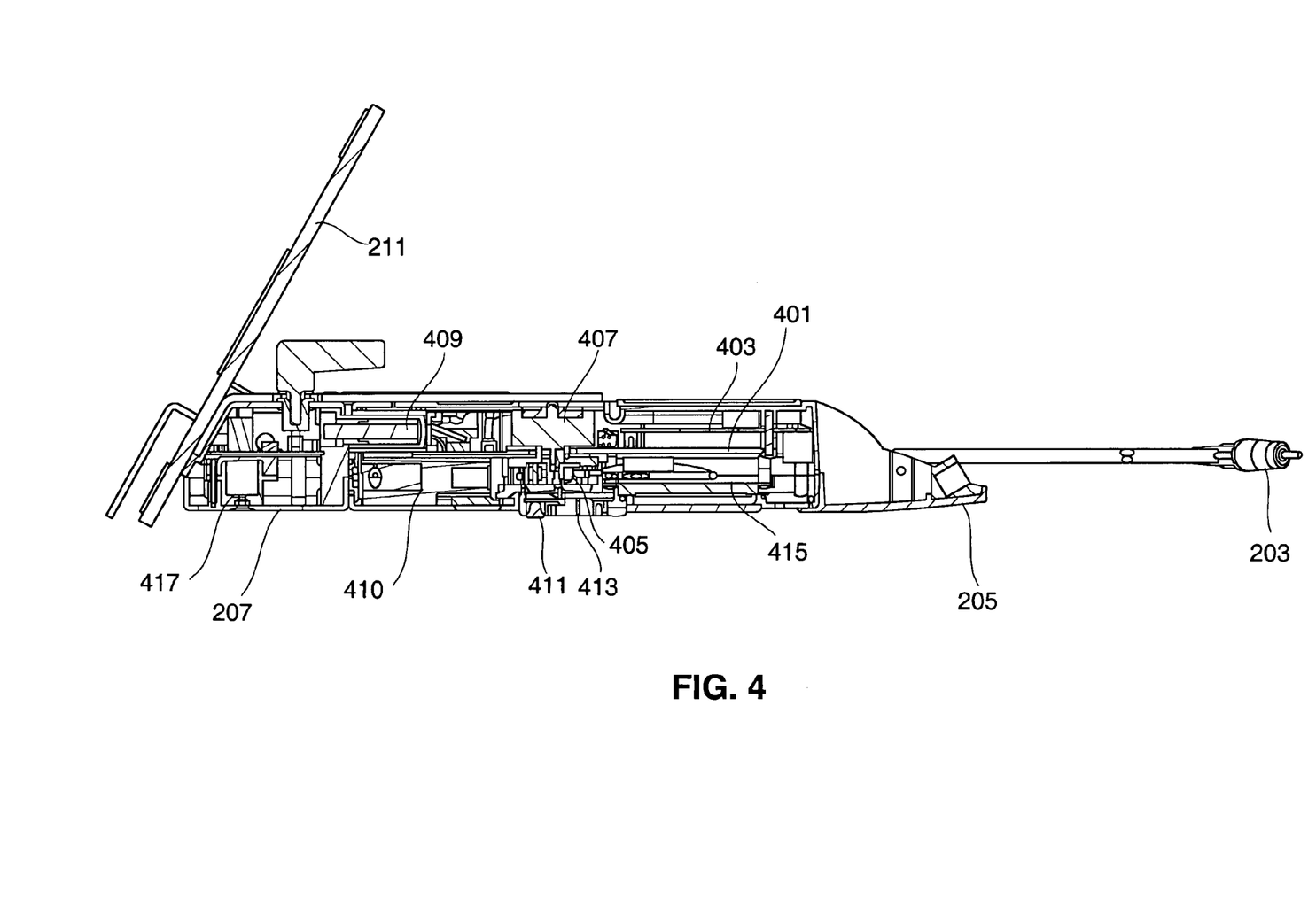
FIG. 4 is a cross-sectional view of the instrument system shown in FIG. 2.
Figure 5:
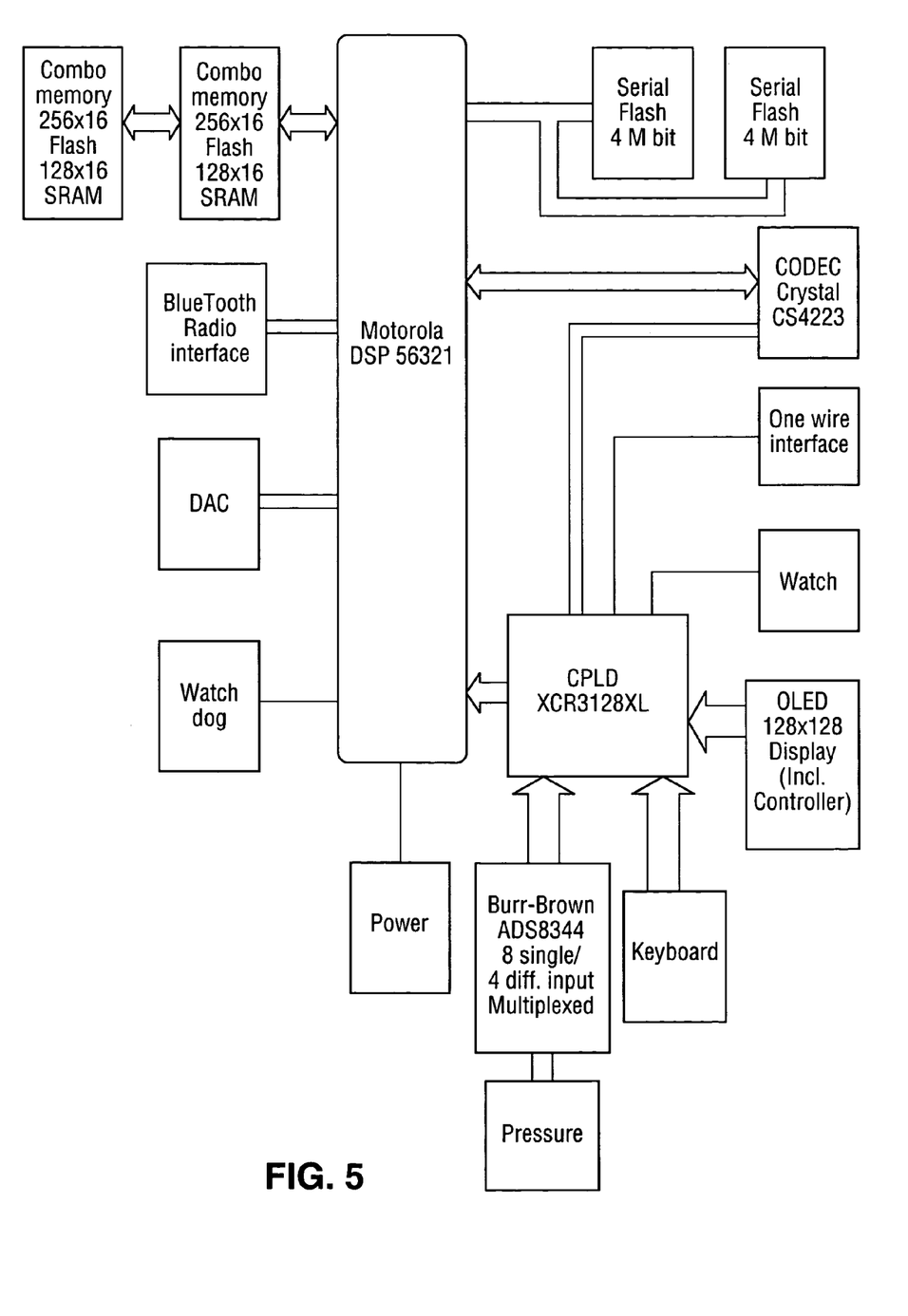
FIG. 5 illustrates a controller/interface portion of a preferred embodiment of the invention.
Figure 6:
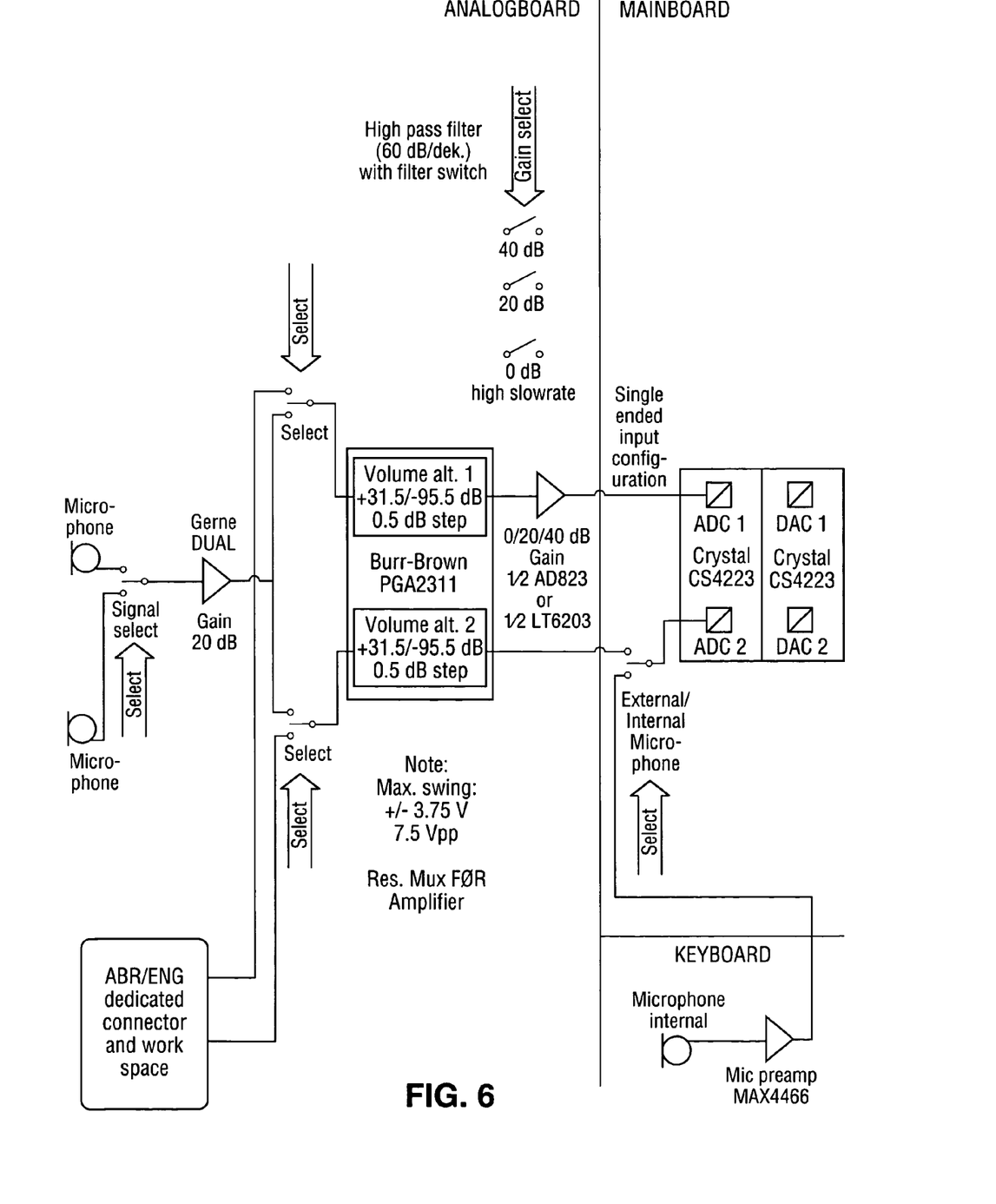
FIG. 6 illustrates an analog input portion of a preferred embodiment of the invention.
Figure 7:
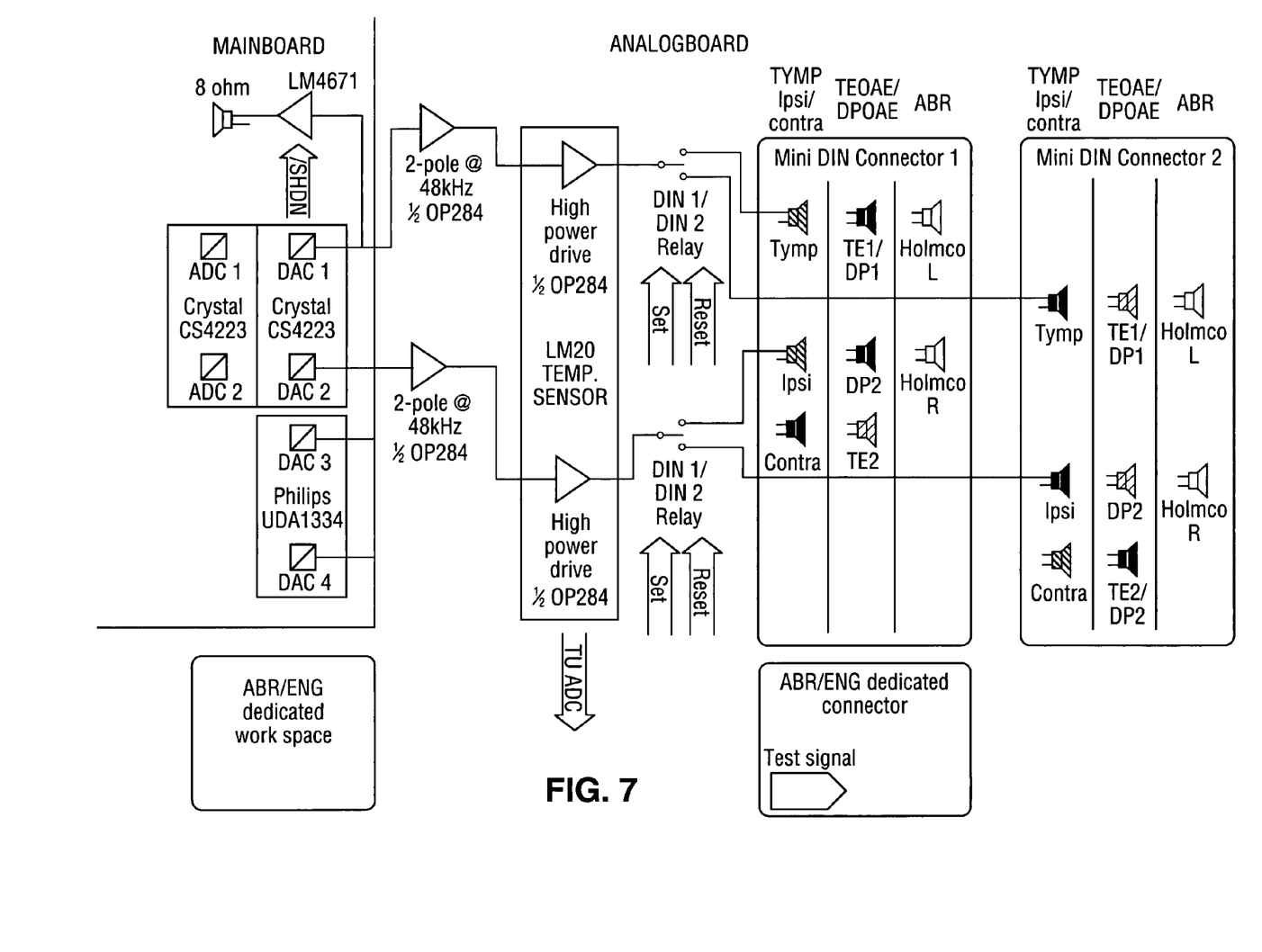
FIG. 7 illustrates an analog output portion of a preferred embodiment of the invention.
Figure 8A:
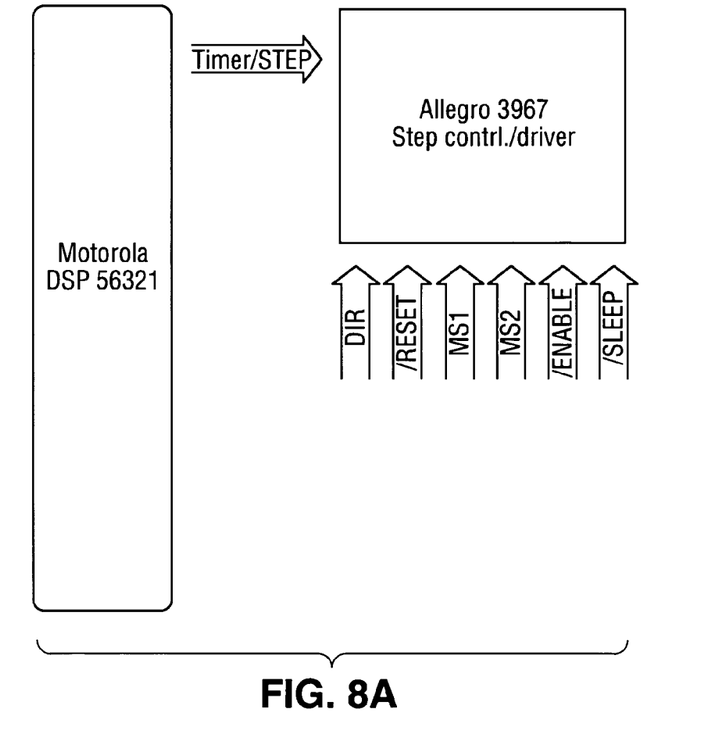
FIGS. 8A-C illustrate a pressure subsystem portion of a preferred embodiment of the invention.
Figure 8B:
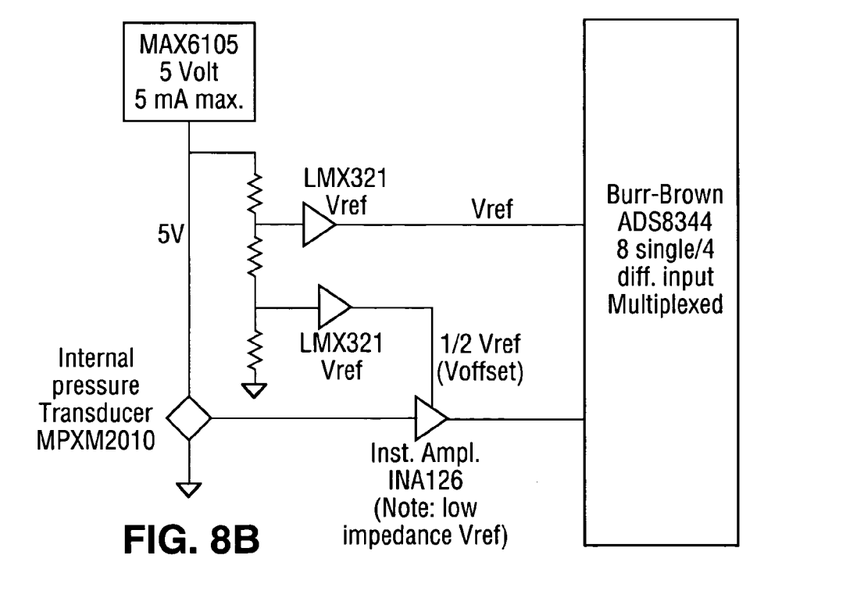
Figure 8C:
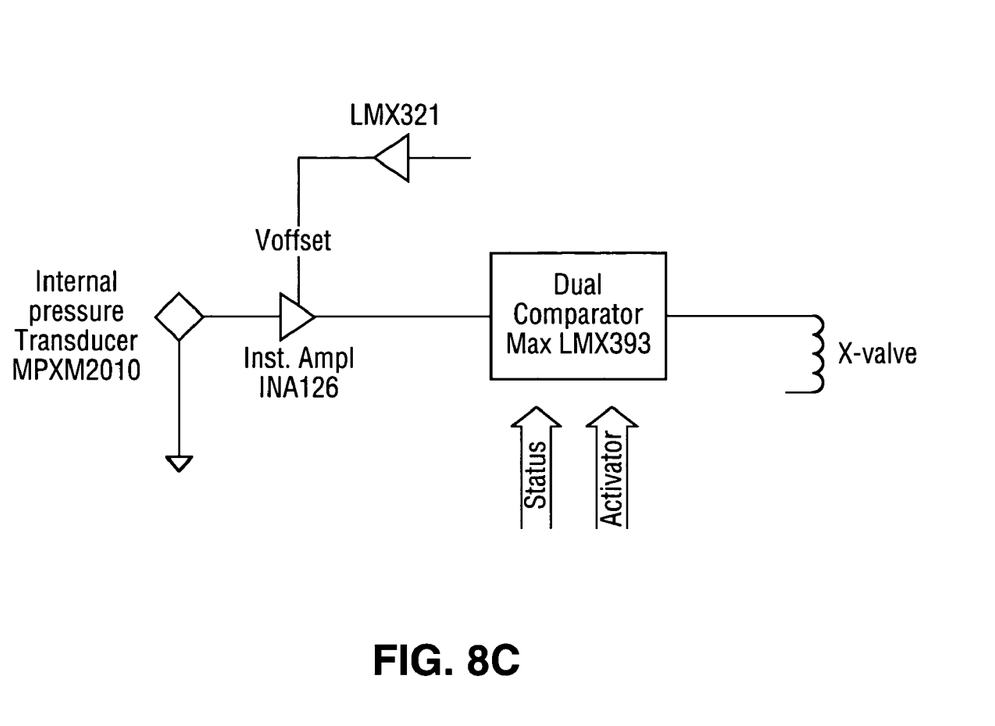
Figure 9:
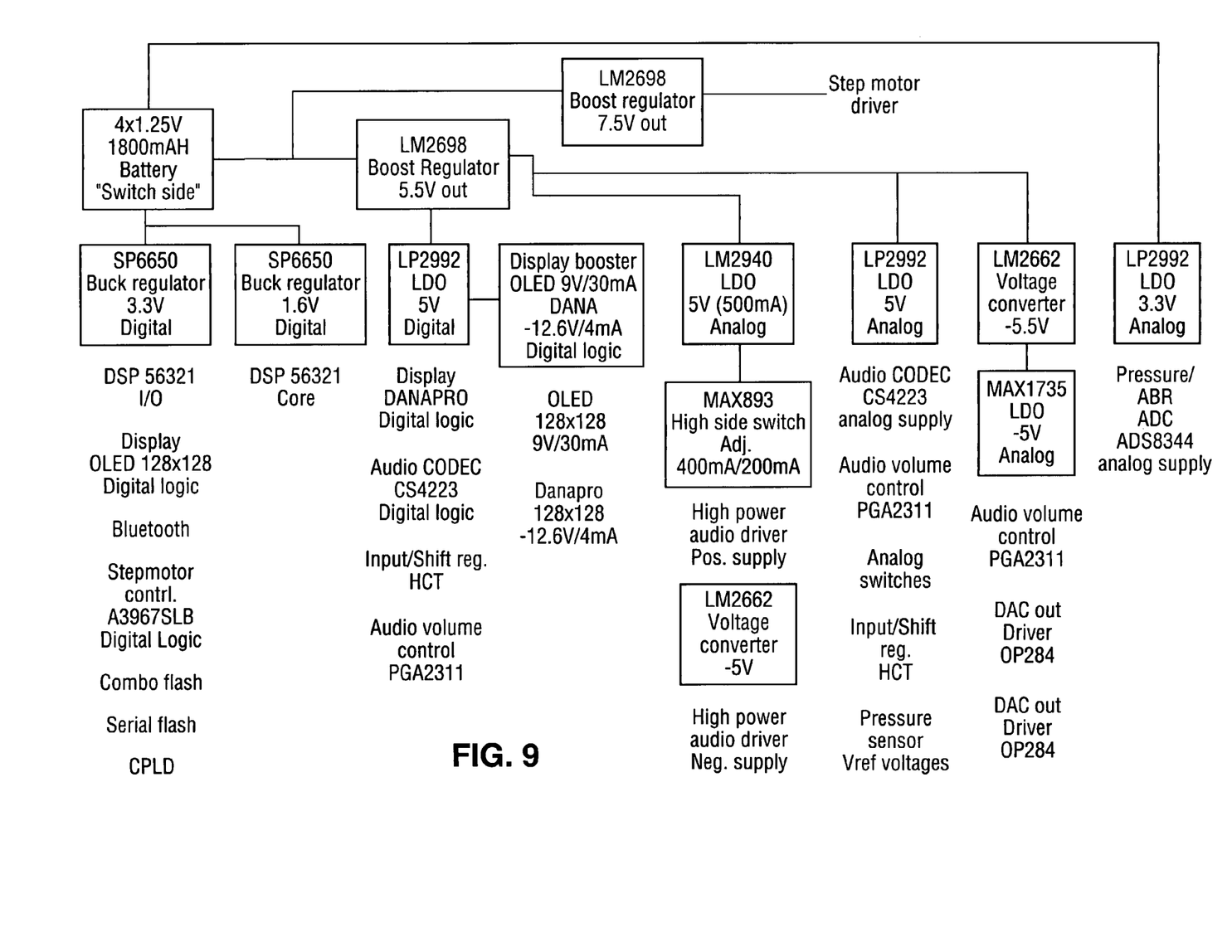
FIG. 9 illustrates a power subsystem portion of a preferred embodiment of the invention.

FIGS. 2-4 illustrate a preferred embodiment of the invention. FIG. 2 is a perspective view of an instrument system 200 while FIG. 3 is a side view of the same instrument system. As shown, instrument system 200 is comprised of portable test instrument 201 along with a variety of accessories including a probe 203, a probe holder 205, and a charging unit 207. Charging unit 207 includes a cradle portion 209 that aids in holding test instrument 201 within the charging unit. Charging unit 207 can be coupled to a desk stand 211, a wall mount (not shown), or used without a stand.

FIG. 4 is a cross-sectional view of instrument system 200. In addition to the previously identified components, this view further shows the main circuit board 401, the analog circuit board 403, pump 405 along with pump motor 407, charger 207 along with charger dorn 409 and battery chamber 410, keypad 411, scroll wheel 413 and organic LED display 415.

FIGS. 5-9 illustrate portions of a preferred embodiment of the invention. Specifically, these figures illustrate the controller/interface, analog input, analog output, pressure subsystem and power subsystem, respectively. As these figures only represent portions of an embodiment, and as there are countless embodiments of the present invention, these figures will not be described in detail herein.

Further description of some of the principal subsystems of instrument 100 will now be provided. It is understood that such subsystems can be used with instrument 100 regardless of the instrument's housing. For example, such subsystems are applicable to the preferred embodiment shown in FIGS. 2 and 3.

Diagnostic Subsystem

Diagnostic subsystem 105, in conjunction with probe 117, provides the means to test the desired auditory function as well as gather the resultant response data. Preferably subsystem 105 is modular and removably connected within instrument 100, thus allowing the easy removal and replacement of subsystem 105. Accordingly, instrument 100 can be easily repaired and/or reconfigured by simply removing the diagnostic subsystem and replacing it with another. This approach has several advantages. First, it allows a malfunctioning instrument to be easily repaired, even at the end user's location. This, in turn, minimizes instrument downtime and inconvenience to the user. Second, a modular approach allows the user to easily modify the instrument's functionality as the user's needs change. Third, it allows the instrument's functionality to be modified as new auditory tests are devised, testing protocols are changed and/or improved, etc., thus preventing obsolescence of the instrument and minimizing user costs.

As previously noted, instrument 100, and more specifically diagnostic subsystem 105, can be configured to perform a wide variety of audiometric tests. In general, diagnostic subsystem 105 can be configured to offer a range(s) of frequencies and/or discrete frequencies, varying intensities and pressures, thus allowing various hearing disorders to be screened and analyzed. Preferably subsystem 105 also includes a 2 cc calibration cavity 417. As a variety of audiometric tests, and the components needed to perform such tests, are well known by those of skill in the art, a detailed description of each possible configuration of subsystem 105 is not provided herein. Some of the desired testing capabilities of instrument 100 are provided below as a means of illustrating the invention. It will be appreciated, however, that the invention is not limited to these particular tests. Accordingly, some of the auditory tests envisioned by the inventors include:

Middle-Ear Testing

A variety of middle-ear tests can be performed by instrument 100, and more particularly diagnostic subsystem 105, depending upon the desired information, desired instrument cost and complexity, etc. Preferably multiple diagnostic subsystems 105 are used in conjunction with instrument 100 although a single, configurable diagnostic subsystem can also be used, either approach allowing the instrument to be configured to perform simple middle-ear function screening or more thorough middle-ear function diagnostics.

In at least one embodiment, diagnostic subsystem 105 is configured to perform tympanometry tests, preferably providing a number of probe tones (e.g., 266 Hz, 678 Hz, 800 Hz and 1000 Hz). Although diagnostic subsystem 105 can be configured to only provide single frequency testing, preferably multiple frequency testing is provided for, thus allowing the middle-ear resonance frequency to be determined. For tymp sweeps, diagnostic subsystem 105 can be configured to allow user defined pressures (e.g., 50 to 400 daPa/sec or higher), AFAP variable pressure speeds, or both. As a result of being able to apply pressure in a controllable fashion, overpressure or underpressure of the middle-ear can be compensated for during testing.

In at least one embodiment, diagnostic subsystem 105 is configured to perform acoustic reflex tests and determine acoustic reflex thresholds (both for contralateral stimulation and ipsilateral stimulation). Stimuli frequencies and intensities are preferably user definable, selected from frequencies and intensity ranges allowed by diagnostic subsystem 105. Preferably diagnostic subsystem 105 is also configured to perform reflex decay measurements.

In at least one embodiment, diagnostic subsystem 105 is configured to determine pure tone thresholds via air conduction. For example, subsystem 105 can be configured with a number of frequencies within the desired auditory frequency range and exhibiting the desired dynamic range (e.g., 8 frequencies with a dynamic range of 1-120 dB).

In at least one embodiment, diagnostic subsystem 105 is configured to test Eustachian tube functions, preferably allowing the functionality to be tested with either the tympanic membrane intact or perforated.

In at least one embodiment, diagnostic subsystem 105 is configured to test acoustic reflex latency and/or perform Gelle's test.

Other Auditory Testing

In addition to the tests outlined above, diagnostic subsystem 105 can be configured to perform numerous other auditory tests. For example, in at least one embodiment diagnostic subsystem 105 is configured to measure the acoustic impedance of the outer ear under varying pressure conditions. In at least one other embodiment, diagnostic subsystem 105 is used to perform audiometric emission measurements. In this configuration, probe 117 includes at least one transducer to generate the stimulus signals and at least one transducer to measure the emission signal. In at least one other embodiment, diagnostic subsystem 105 is configured to perform advanced audiometry (i.e., HL or SPL). In at least one other embodiment, diagnostic subsystem 105 is configured to perform ABLB, Stenger and SISI special testing. In at least one other embodiment, diagnostic subsystem 105 is configured to perform high frequency audiometry, preferably up to 16 kHz.

User Interface

In its simplest configuration, user interface 109 is used to program the desired test parameters into instrument 100. For example, the various parameters associated with tympanometry and reflex threshold testing can be entered via interface 109. More specifically, user interface 109 can be used select the function/test to be performed as well as whether the function/test is to be performed manually, automatically, automatically using a preprogrammed test sequence, or using a previously user-entered test profile. Additionally, user interface 109 can be configured to allow setting and or selecting; (i) sensitivity scales (e.g., for tympanometry testing), (ii) tone or frequency, (iii) single versus multiple tones, (iv) tone presentation timing, (v) Eustachian tube testing mode (e.g., perforated vs. non-perforated tympanic membrane), (vi) pressure, etc.

In at least one embodiment, user interface 109 is used to set-up the basic operation of instrument 100. For example, user interface 109 can be used to select the instrument's operational language, the format for displaying test results (e.g., graphical versus tabular, side by side displays of data, overlaying data, etc.), configuration of user input means 111, configuration of display means 113, enable/disable time and/or date stamping of test data, and configuration/control of wireless communication subsystem 121.

In a preferred embodiment of the invention, user interface 109 is used to enter and/or access individual patient data (e.g., patient profile, previous test data, etc.). Preferably interface 109 can also be used to enter and/or access various office management tools such as patient appointment schedules, patient contact information, and/or patient billing information (e.g., payment history).

Input means 111 can use any combination of buttons, switches, rotating/scrolling wheels, etc. In at least one embodiment, input means 111 includes a virtual keyboard, preferably an alphanumeric keyboard, graphically displayed on display means 113. Individual keys of the virtual keyboard are 'struck' (i.e., pushed, entered, accessed, etc.) either through the use of a touch sensitive display means or by a combination of key selection buttons (e.g., arrow keys) and an enter button. In at least one other embodiment, input means 111 also includes at least one microphone for use in dictating (e.g., recordable in memory 115), preparing voice files for attachment to test data or for communicating with office personnel, etc.

In at least one embodiment display means 113 is used to provide the user with various types of information relating to both the configuration and functionality of instrument 100. For example, display means 113 can be used in conjunction with input means 111 to configure instrument 100 (e.g., selection of interface language), configure wireless communication subsystem 121, monitor the performance of instrument 100 (e.g., battery charge level), select an auditory test, and select the desired test parameters. In a preferred embodiment, display means 113 is used to communicate test results, either textually or graphically, to the user. In another preferred embodiment, display 113 is used to present the user with patient data (e.g., patient profile, previous test data, etc.) and/or office management information (e.g., appointment schedules, patient and/or supplier contact information, invoice information, etc.).

In at least one embodiment, display 113 includes a touch sensitive screen, thus allowing the display to also function as input means 111.

Display means 113 can utilize various screen sizes and resolutions, depending upon power system constraints, expected tests, desired presentation formats, etc. Preferably display means 113 uses organic light emitting diodes (OLED), although other types of technology can be used. For example, display 13 can use liquid crystal display (LCD) technology, light emitting polymers (LEP), electroluminescent (EL) or active matrix electroluminescent (AMEL) technology, organic thin film transistors (organic TFT), amorphous silicon integrated displays (ASID), pliable display technology (PDT) or any other display technology that can provide a suitable resolution in the desired display size.

Probes

Depending upon the desired configuration, probe 117 can be coupled to instrument either directly or via a probe cable 119. One benefit of coupling probe 117 directly to instrument 117 is to achieve an extremely compact device. One benefit of coupling probe 117 via cable 119 is to provide the patient with a light-weight probe that does not overly constrict patient movement.

Although instrument 100 can use standard probes, in a preferred embodiment probe 117 is an intelligent probe. As used herein, intelligent probe is defined as a probe that includes the ability to communicate probe information to the instrument to which it is attached (e.g., instrument 100) in addition to that information commonly communicated via a probe such as stimulus signals and response data.

In at least one embodiment, the probe information communicated via the intelligent probe is calibration data. Calibration data can include data about the probe, which is then used by diagnostic subsystem 105 and/or processor 107 to insure proper instrument set-up. Calibration data can also include a date stamp, thus allowing instrument 100 to notify the user when the date stamp indicates that the calibration data is no longer valid.

In at least one embodiment, the probe information communicated via the intelligent probe is probe configuration data. Probe configuration data can include information about the capabilities of the probe, thus allowing the diagnostic subsystem to be properly set-up. Preferably diagnostic subsystem set-up is performed automatically upon connecting probe 117 to instrument 100. Such automatic set-up is sometimes referred to as a plug and play capability.

In at least one embodiment, the probe information communicated via the intelligent probe is system operation information. For example, one or more buttons or other types of input means 131 can be included in the body of probe 117, the buttons allowing test sequences to be initiated and/or stopped without the use of input means 111 on instrument 100. Preferably buttons 131 on probe 117 duplicate one or more buttons/input means 111 on instrument 100. In another example of system operation information that can be communicated via the intelligent probe, one or more LEDs or other types of display means 133 can be included in the body of probe 117. Preferably LEDs/display means 133 provide status information to the user (e.g., test sequence initiating, test sequence complete, etc.).

Processor and Memory

Processor 107, in conjunction with memory 115, provides for instrument 100's functionality (e.g., implement tests, analyze test results, manage instrument operation, etc.). As previously noted, instrument 100 can utilize a single processor or multiple processors. For example, diagnostic subsystem 105 can utilize a dedicated processor while a different processor can control the overall operation of the instrument. Accordingly, processor 107 in FIG. 1 is only intended to represent the processing capabilities of instrument 100.

Memory 115 is preferably used to store information relating to the instrument's testing capabilities. For example, test sequences and parameters can be stored in memory 115. These test sequences and parameters can be factory installed and/or user installed and in the case of the latter, are preferably indexable by user, test type and/or patient. Memory 115 can also be used to store test profiles, including probe requirements if probe 117 is an intelligent probe as previously disclosed.

In at least one embodiment, memory 115 is used to store test data, preferably including both current test results and previous test results (assuming that the patient has previous test results). Memory 115 can also be used to store standardized test results, thus providing an easy means of gauging a patient's test results. For example, standardized test results can be based on a segment of the population (e.g., persons within a predefined age group), based on achieving a certain performance level (e.g., superior, average, below average), based on achieving a percentage of what is considered average performance, etc.

In at least one embodiment, memory 115 is used to store data and information generally relating to the user's office, and more specifically relating to the management of the user's office and professional practice. This data is accessible, and modifiable, through use of input means 111 and displayable through the use of display means 113. Examples of such data and information are patient profiles, including personal data, medical data, past test results, billing information, etc. Other examples of data and information that can be stored in memory 115 are employee files, appointment records, supply records and payroll records.

Short Range Wireless Communication Subsystem

Instrument 100 includes a short distance wireless networking subsystem 121 that provides short distance wireless communications between instrument 100 and a correspondingly enabled peripheral electronic device or system (e.g., devices/systems 123-125 in FIG. 1). Preferably short distance wireless networking subsystem 121 has a range on the order of 30 feet or less, more preferably on the order of 100 feet or less, still more preferably on the order of 500 feet or less, and yet still more preferably on the order of 1000 feet or less.

Short distance wireless networking subsystem 121 includes a transceiver 127 and can utilize any of a variety of networking technologies and protocols, as long as the selected system provides suitable networking capabilities between instrument 100 and the desired device or system (e.g., devices/systems 123-125). Examples of suitable technologies and standards include Bluetooth and IEEE802.11. As such technologies and standards are well know in the art (see, for example, the specifications found at www.bluetooth.com, www.standards.ieee.org/getieee802/802.11.html and www.grouper.ieee.org/groups/802/11/, all of which are incorporated herein by reference), further description will not be provided herein. Subsystem 121, which is coupled to an appropriate antenna, controls the communication of data between instrument 100 and the desired device or system.

Due to the inclusion of wireless networking subsystem 121, instrument 100 can communicate with any similarly enabled device. For example, if the user of instrument 100 wants to make a hard copy of some test results, the test results can be sent to a printer (e.g., device 124) which is enabled (e.g., using a Bluetooth adaptor). If the user wants to construct on-screen audiograms in real time, and assuming instrument 100 is NOAH compatible as it is in a preferred embodiment, test data can be feed directly to an enabled PC database via wireless networking module 121. In an alternate example, wireless networking subsystem 121 can be used to communicate data (e.g., patient data, office management data, etc.) between instrument 100 and either an enabled computer (e.g., device 123) or an enabled local area network (LAN) (e.g., system 125) or another similarly enabled device (e.g., facsimile devices, personal digital assistants, cellular telephones, etc.). In yet another example, assuming that instrument 100 includes a schedule (e.g., appointment schedule, personal schedule, etc.), wireless networking subsystems 121 can be used to send a reminder such as an e-mail, voice message (e.g., using a voice file or a voice synthesis system), or other reminder to an appropriately enabled receiver (e.g., enabled personal digital assistant, enabled cellular phone, etc.). It will be appreciated that the above examples of the possible uses for wireless networking subsystem 121 are meant to be illustrative only and that the present invention is not limited to these applications.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. An auditory test instrument comprising:
   a connector configured to connect to at least one test probe;
   a power supply for supplying power to the test instrument, wherein said power supply is portable;
   a wireless networking subsystem configured to wirelessly transmit first signals via a short distance wireless network to a peripheral electronic device or system;
   a diagnostic subsystem coupled to said at least one test probe, said diagnostic subsystem configured to implement at least one auditory diagnostic test;
   input means configured to accept commands from a user;
   a display configured to display results from said at least one auditory diagnostic test; and
   at least one processor coupled to said diagnostic subsystem and to said input means;
   wherein the auditory test instrument further comprises a housing containing the diagnostic subsystem, the peripheral electronic device or system is external to the housing, and the wireless network subsystem is configured to transmit the first signals to the peripheral electronic device or system that is external to the housing.

2. The auditory test instrument of claim 1, wherein said at least one probe is detachably coupled to said auditory test instrument.

3. The auditory test instrument of claim 1, wherein said at least one probe is an intelligent probe.

4. The auditory test instrument of claim 1, wherein said power supply is rechargeable.

5. The auditory test instrument of claim 1, wherein said power supply is rechargeable via a contactless recharging system.

6. The auditory test instrument of claim 1, wherein said wireless networking subsystem is further adapted to receive second signals via said short distance wireless network from said peripheral electronic device.

7. The auditory test instrument of claim 1, wherein said wireless networking subsystem is a Bluetooth enabled wireless networking subsystem and wherein said peripheral electronic device or system is a Bluetooth enabled electronic device or system.

8. The auditory test instrument of claim 1, wherein said peripheral electronic device or system is a LAN system.

9. The auditory test instrument of claim 1, wherein said peripheral electronic device or system is a device selected from the group of devices consisting of computers, personal digital assistants, printers, facsimile devices, and cellular telephones.

10. The auditory test instrument of claim 1, wherein said diagnostic subsystem is modular and detachable.

11. The auditory test instrument of claim 1, wherein said diagnostic subsystem is configured to perform at least one middle-ear test.

12. The auditory test instrument of claim 1, wherein said diagnostic subsystem is configured to perform at least one test selected from the group of tests consisting of tympanometry, tympanometry sweeps, acoustic reflex, acoustic reflex threshold determination, reflex decay measurements, pure tone thresholds, Eustachian tube function, acoustic reflex latency, Gelle's test, outer ear acoustic impedance under varying pressures, audiometric emission measurements, advanced audiometry, ABLB, Stenger and SISI tests.

13. The auditory test instrument of claim 1, wherein said commands accepted by said input means configure said diagnostic subsystem.

14. The auditory test instrument of claim 1, wherein said commands accepted by said input means configure said auditory test instrument.

15. The auditory test instrument of claim 1, further comprising a memory, wherein said commands accepted by said input means select a test profile stored in said memory.

16. The auditory test instrument of claim 1, further comprising a memory, wherein said commands accepted by said input means provide access to patient data stored in said memory.

17. The auditory test instrument of claim 1, further comprising a memory, wherein said commands accepted by said input means provide access to office management tools stored in said memory.

18. The auditory test instrument of claim 1, wherein said display is selected from the group of displays consisting of liquid crystal displays, light emitting polymer displays, electroluminescent displays, active matrix electroluminescent displays, organic thin film transistor displays, organic light emitting diode displays, amorphous silicon integrated displays, and pliable display technology displays.

19. The auditory test instrument of claim 1, wherein the housing has an opening, and wherein the display is located within the opening of the housing.

20. The auditory test instrument of claim 19, wherein the input means is located adjacent to the display, and the input means and the display are integrated with the housing.

21. The auditory test instrument of claim 19, further comprising a medium inside the housing for storing a result or the at least one auditory diagnostic test.

22. The auditory test instrument of claim 1, wherein the connector is configured to detachably connect to the at least one test probe.

23. The auditory test instrument of claim 1, wherein the at least one test probe is mainly for use in hearing test(s).

24. The auditory test instrument of claim 1, wherein the peripheral electronic device or system is separate from the auditory test instrument, and the auditory test instrument is configured to communicate with the peripheral electronic device or system using the wireless networking subsystem.

25. An auditory test instrument comprising:
   a connector configured to connect to at least one test probe;
   a power supply for supplying power to the test instrument, wherein said power supply is portable;
   a wireless networking subsystem adapted to wirelessly transmit first signals via a short distance wireless network to a peripheral electronic device or system;
   a diagnostic subsystem coupled to said at least one test probe, said diagnostic subsystem configured to implement at least one auditory diagnostic test;

input means configured to accept commands from a user;
a display configured to display results from said at least one auditory diagnostic test; and
at least one processor coupled to said diagnostic subsystem and to said input means;
wherein said at least one probe further comprises a memory, wherein calibration data is stored in said memory, said calibration data automatically communicated to said auditory test instrument upon coupling said at least one probe to said auditory test instrument and providing power to said auditory test instrument.

26. An auditory test instrument comprising:
a connector configured to connect to at least one test probe;
a power supply for supplying power to the test instrument, wherein said power supply is portable;
a wireless networking subsystem adapted to wirelessly transmit first signals via a short distance wireless network to a peripheral electronic device or system;
a diagnostic subsystem coupled to said at least one test probe, said diagnostic subsystem configured to implement at least one auditory diagnostic test;
input means configured to accept commands from a user;
a display configured to display results from said at least one auditory diagnostic test; and
at least one processor coupled to said diagnostic subsystem and to said input means;
wherein said at least one probe further comprises a memory, wherein probe configuration data is stored in said memory.

27. The auditory test instrument of claim 26, wherein said probe configuration data is automatically communicated to said diagnostic subsystem and wherein said at least one auditory diagnostic test is automatically selected in response to said probe configuration data.

28. An auditory test instrument comprising:
a housing having a hand-held size;
a connector configured to couple to at least one test probe;
a power supply for supplying power to the test instrument, wherein said power supply is portable, and wherein said power supply is rechargeable via a contactless charging unit;
a wireless networking subsystem configured to wirelessly transmit first signals via a short distance wireless network to a peripheral electronic device or system, and configured to receive second signals via said short distance wireless network from said peripheral electronic device or system;
a diagnostic subsystem located within said housing and coupled to said at least one test probe, said diagnostic subsystem configured to implement at least one middle-ear test;
input means configured to accept commands from a user;
a display integrated with said housing and configured to display results from said at least one middle-ear test;
at least one processor located within said housing and coupled to said diagnostic subsystem and to said input means; and
a memory located within said housing and coupled to said at least one processor, said memory storing testing profiles, patient data and office management tools;
wherein the peripheral electronic device or system is external to the housing, and the wireless network subsystem is configured to transmit the first signals to the peripheral electronic device or system that is external to the housing.

29. The auditory test instrument of claim 22, wherein said peripheral electronic device or system is a device or system selected from the group consisting of local area networks, computers, personal digital assistants, printers, facsimile devices, and cellular telephones.

30. The auditory test instrument of claim 28, wherein the connector is configured to detachably couple to the at least one test probe.

31. The auditory test instrument of claim 28, wherein the at least one test probe is mainly for use in hearing test(s).

32. The auditory test instrument of claim 28, wherein the peripheral electronic device or system is separate from the auditory test instrument, and the auditory test instrument is configured to communicate with the peripheral electronic device or system using the wireless networking subsystem.

* * * * *